United States Patent [19]

Heckele

[11] Patent Number: 5,324,283
[45] Date of Patent: Jun. 28, 1994

[54] MEDICAL INSTRUMENT HAVING A SWITCH FOR CONTROLLING AN EXTERNAL DEVICE

[75] Inventor: Helmut Heckele, Knittlingen, Fed. Rep. of Germany

[73] Assignee: Richard Wolf GmbH, Knittlingen, Fed. Rep. of Germany

[21] Appl. No.: 891,511

[22] Filed: Jun. 1, 1992

[30] Foreign Application Priority Data

Jul. 3, 1991 [DE] Fed. Rep. of Germany ....... 4121977

[51] Int. Cl.⁵ ............................................. A61B 17/36
[52] U.S. Cl. ...................................... 606/15; 385/19; 606/16; 128/4
[58] Field of Search ......................... 385/19; 128/4, 6; 606/15, 16, 4, 7

[56] References Cited

U.S. PATENT DOCUMENTS

| | | | |
|---|---|---|---|
| 4,505,539 | 3/1985 | Auracher et al. | 385/19 |
| 4,836,636 | 6/1989 | Obara et al. | 385/19 |
| 4,939,336 | 7/1990 | Meyer et al. | 606/7 |
| 5,003,965 | 4/1991 | Talish et al. | |
| 5,004,318 | 4/1991 | Ohashi | 385/19 |
| 5,073,001 | 12/1991 | Sato et al. | 385/19 |
| 5,122,135 | 6/1992 | Dürr et al. | 606/4 |
| 5,163,112 | 11/1992 | Lefevre et al. | 385/19 |

FOREIGN PATENT DOCUMENTS 1840499 11/1961 Fed. Rep. of Germany.
3409944 9/1985 Fed. Rep. of Germany.
3822311 12/1989 Fed. Rep. of Germany.

*Primary Examiner*—Peter A. Aschenbrenner
*Attorney, Agent, or Firm*—Panitch Schwarze Jacobs & Nadel

[57] ABSTRACT

A medical instrument has a switch for controlling the operation of an external device operatively connected to the switch by way of a control section. The control section is a light transmitting section extending between a light source and a light receiver, and includes two optical fibers extending within the instrument with their ends in opposed spaced relationship. A cover plate is movable by means of a switch button, between the opposed ends of the fibers to alter the transmission of light to the light receiver at least in order to switch the external device on and off.

6 Claims, 1 Drawing Sheet

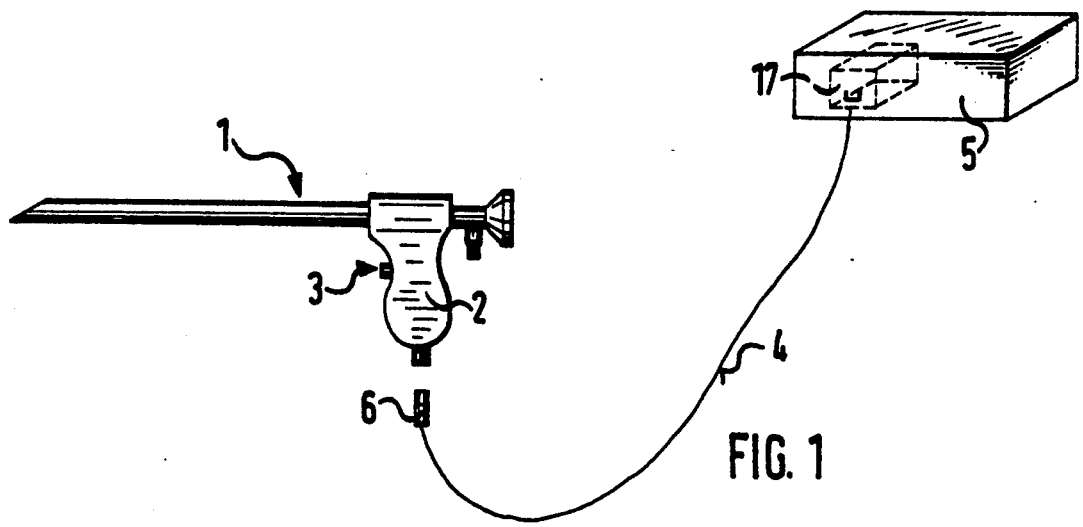
FIG. 1
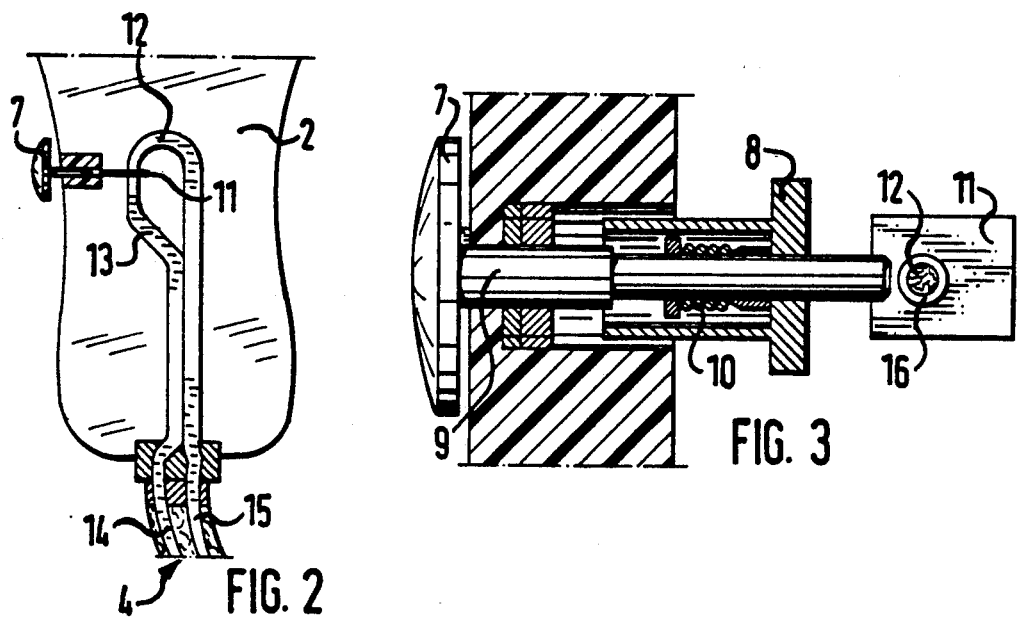
FIG. 2
FIG. 3
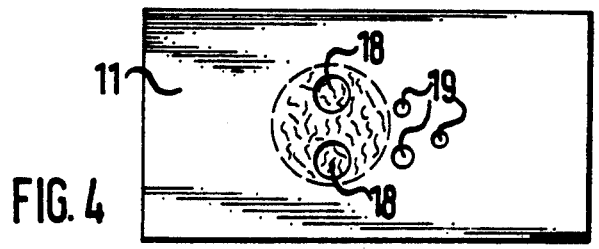
FIG. 4

MEDICAL INSTRUMENT HAVING A SWITCH FOR CONTROLLING AN EXTERNAL DEVICE

FIELD OF THE INVENTION

The invention relates to a medical instrument having a switch for controlling the operation of an external device operatively connected to the switch by way of a control section.

During endoscopic surgery, use is often made, from time to time, of accessory devices such as high-frequency coagulators, laser devices, and electrically operated flushing and/or suction devices which are usually activated or deactivated by means of pedal switches. It is known, however, to build switches into the handles of medical instruments.

BACKGROUND OF THE INVENTION

German Utility Model No. 1 840 499 discloses a switch built into the handle of a resectoscope for opening and closing the high-frequency circuit. The switch is operated with the thumb of the hand grasping the handle.

A disadvantage of such built-in switches is that their mechanisms can be impaired by the temperatures occurring during sterilisation of an instrument, and such mechanisms may be damaged by the ingress of water thereinto. Also, with such instruments with which a coagulator is used the electrical potential of the coagulator is applied to the input wires of the handle and to the switch contacts so long as the coagulator is switched on. Comprehensive means must, therefore, be provided for electrically insulating the switch and the switch housing, that is to say, basically the handle, in order to safeguard the patient and the operator.

SUMMARY OF THE INVENTION

It is, therefore, an object of the invention to provide a medical instrument having a manually operated switch for accessory devices used in endoscopic surgery, the switch mechanism being robust and insensitive to the effects of temperature and moisture and the danger of accidental leakage of current being avoided.

According to the present invention, therefore, the control section is light transmitting and extends between a light source and a light receiver and partially through the instrument. The output of the light receiver controls the operation of the external device, and the light beam arriving at the light receiver along the light transmitting control section is altered by means of the switch in such a way that the external device can at least be switched on and off.

BRIEF DESCRIPTION OF THE DRAWINGS

FIG. 1 is a schematic side view of a medical instrument having a switch for controlling the operation of an external accessory device, according to an embodiment of the invention;

FIG. 2 is a schematic sectional view of the switch when in a switched-on state,

FIG. 3 is an enlarged side view, shown partly in section, of the switch according to FIG. 2; and FIG. 4 is an enlarged view of a cover plate of a switch according to an alternative embodiment.

DETAILED DESCRIPTION OF EMBODIMENTS OF THE INVENTION

A switch 3 for a medical instrument is, as shown in FIG. 1, built, for example, into the handle 2 of an endoscope 1. The handle 2 is connected by way of a flexible optical fiber cable 4 to an external accessory device 5 which may be, for example, an electrically operated flushing or suction device. The optical fiber cable 4 can be coupled to the endoscope 1 by means of an optical plug-and socket connection 6.

The switch 3 includes, as shown in FIG. 3, a control button 7 having a shaft 9 which is longitudinally slidable in a holder 8. The control button 7 is urged towards an extended, rest position by means of a spring 10 acting on the shaft 9. The shaft 9 is connected at its end remote from the control button 7 to a planar cover plate 11 which is accordingly displaceable by operation of the control button 7 in the direction of movement thereof. As shown in FIG. 2, the cover plate 11 is guided in a plane on either side of which end respective optical fibers 12 and 13, of the cable 4, these ends of the fibers 12 and 13 being exactly opposite to each other. The optical fibers 12 and 13 are connected to the socket of the plug and socket connection 6 and extend into the optical fiber cable 4 as a return line 15 and a supply line 14, respectively when the plug and socket are mated. The cover plate 11 is made of an opaque material but comprises a light-transmitting region 16 which can be aligned with said ends of the optical fibers 12 and 13 by pushing the control button 7 in.

The accessory device 5 includes, in addition to a pump (not shown), a control unit 17 which essentially contains a light source and a light receiver as well as a suitable analyser circuit for received light signals. The optical fiber cable 4 is connected to the accessory device 5 in such a way that the supply line 14 is associated with the light source and the return line 15 with the light receiver.

The plug and socket being mated, the operation of the instrument 1 provided with the switch 3 is as follows. On switching on the control unit 17, light passes from said light source of the unit 17 by way of the supply line 14 (FIG. 2) and the optical fiber 13 extending into the handle 2, to the end of the optical fiber 13 located adjacent to cover plate 11. In the rest position of the control button 7 of the switch 3, the portion of the cover plate 11 with which the end of the fiber 13 is aligned is non-light-transmitting, so that the light beam is blocked. When the control button 7 is pushed in, the cover plate 11 is advanced so that its light-transmitting region 16 is aligned with the ends of the optical fibers 12 and 13 (FIG. 3), so that the light beam enters the opposed end of the optical fiber 12 and thus passes through the optical fiber cable 4 into said light receiver in the control unit 17. The signal received by the light receiver is processed by the control unit 17 which causes the accessory device 5 to be switched on in a preferred circuit of the control unit 17 on receiving a predetermined quantity of light, whereas the accessory device 5 is switched off if a light signal fails to appear at the light receiver.

According to a further embodiment of the invention the light-transmitting region 16 of the plate 11 may be such that not only can the device 5 be switched "off" and "on", but switching as a function of the quantity of light received by the light receiver can also be carried out. To this end, the cover plate 11 as shown in FIG. 4 is divided into regions respectively allowing the passage of a greater or lesser quantity of light. This can be achieved, for example, by providing the cover plate 11 with openings 18 and 19 of different sizes. In this case the switch 1 must have different corresponding switch positions which are distinguishable by the operator. By virtue of this embodiment of the switch 3, accessory devices 5 may be regulated according to the quantity of light arriving at the light receiver at any given time, or different accessory devices 5 may be switched on and off according to said quantity of light. Further the cover plate 11 may be coded by a particular arrangement of the openings 18 and 19 in order to enable different accessory devices 5 to be switched simultaneously.

What is claimed is:

1. A medical instrument having a switch for controlling the operation of an external device which can be switched on and off, comprising a light transmitting section which extends into the instrument, the switch being adapted to alter the transmission of light through the light transmitting section at least for the purpose of switching an external device on and off, said light transmitting section comprising optical fibers, having first ends in the medical instrument, which ends are disposed opposite to each other in spaced relationship, one of the fibers having a second end from which light is transmitted to the first end thereof, and the other optical fiber having a second end to which light is transmitted from the first end thereof, a cover plate being displaceable by means of the switch, between said first ends of the fibers to vary the transmission of light through the fibers, said cover plate comprising regions allowing the transmission of different quantities of light.

2. An instrument as claimed in claim 1, wherein a control button connected to the cover plate, is connected to a shaft mounted for longitudinal movement in the switch against the action of a spring.

3. An instrument as claimed in claim 1, wherein the cover plate comprises at least one light transmitting region and one opaque region.

4. An instrument as claimed in claim 2, wherein the cover plate is urged by the spring into a rest position in which the cover plate interrupts the transmission of light through the optical fibers.

5. An instrument as claimed in claim 1, wherein the cover plate is formed with openings of different sizes.

6. An instrument as claimed in claim 1, further comprising a flexible optical fiber cable comprising a supply line and a return line, and a plug and socket connection connected to said cable and which is connectable to said second ends for supplying light to and returning light from said light transmitting section.

* * * * *